US00PP23342P3

(12) United States Plant Patent
Egger

(10) Patent No.: US PP23,342 P3
(45) Date of Patent: Jan. 22, 2013

(54) ***ACANTHUS* PLANT NAMED 'WHITEWATER'**

(50) Latin Name: ***Acanthus* spp.**
Varietal Denomination: Whitewater

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 377 days.

(21) Appl. No.: 12/798,838

(22) Filed: Apr. 12, 2010

(65) Prior Publication Data

US 2011/0252528 P1 Oct. 13, 2011

(51) Int. Cl.
*A01H 5/00* (2006.01)

(52) U.S. Cl. ..... Plt./263.1; Plt./373

(58) Field of Classification Search ..... Plt./373, Plt./263.1
See application file for complete search history.

(56) References Cited

U.S. PATENT DOCUMENTS

PP4,516 P * 4/1980 Engelmann ..... Plt./373
PP4,602 P * 10/1980 Cobia ..... Plt./373

OTHER PUBLICATIONS

UPOV ROM GTITM Computer Database, GTI Jouve Retrieval Software 2011/10 Citation for 'Whitewater'.*

Anonymous Bear's Breeches *Acanthus* 'Whitewater' from Saunders Brothers Inc. Available at http://www.saundersbrothers.com accessed Sep. 30, 2011.*

* cited by examiner

*Primary Examiner* — Wendy C Haas

(74) *Attorney, Agent, or Firm* — Klarquist Sparkman, LLP

(57) ABSTRACT

A new and distinct form of *Acanthus* plant characterized by variegated leaves and excellent vigor.

2 Drawing Sheets

Botanical denomination: *Acanthus* spp.
Variety designation: 'Whitewater'.
Parentage: *Acanthus*×'Summer Beauty'×*Acanthus mollis* TASMANIAN ANGEL®.

BACKGROUND OF THE INVENTION

The present invention relates to a new and distinct cultivar of *Acanthus*, given the name, 'Whitewater'. *Acanthus* is in the family Acanthaceae. This new variety originated from a planned cross between *Acanthus*×'Summer Beauty' (an unpatented plant) as the seed parent and *Acanthus mollis* TASMANIAN ANGEL® (an unpatented plant) as the pollen parent. Compared to the seed parent, *Acanthus*×'Summer Beauty', the new cultivar has variegated leaves and pink tinted flowers and bracts rather than unvariegated leaves and white flowers with purple bracts. Compared to the pollen parent, *Acanthus mollis* TASMANIAN ANGEL® the new cultivar has a much more vigor, longer leaves, and taller flowers. Grown side by side under the same conditions *Acanthus* 'Whitewater' at 18 months from tissue culture will have double the plant spread and taller flower spikes than *Acanthus mollis* TASMANIAN ANGEL®. Two-year-old plants of *Acanthus* 'Whitewater' will not go fully dormant overwinter in Canby, Oreg. and will be of larger size than *Acanthus mollis* TASMANIAN ANGEL®.

While *Acanthus mollis* TASMANIAN ANGEL® is a very nice variegated plant, it does not have very much vigor. It often fails to return after one winter when grown outside. In USDA zone 8 it fails to thrive. *Acanthus*×'Summer Beauty' has very good hardiness and heat tolerance and grows as well in the southern US as in Oregon. This new *Acanthus* has the good characteristics of both parents and it is distinct in its combination of variegated leaves and excellent vigor.

The new variety has been reproduced only by asexual propagation (division and micropropagation), using the normal organ method where tip and lateral buds are cultured. Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
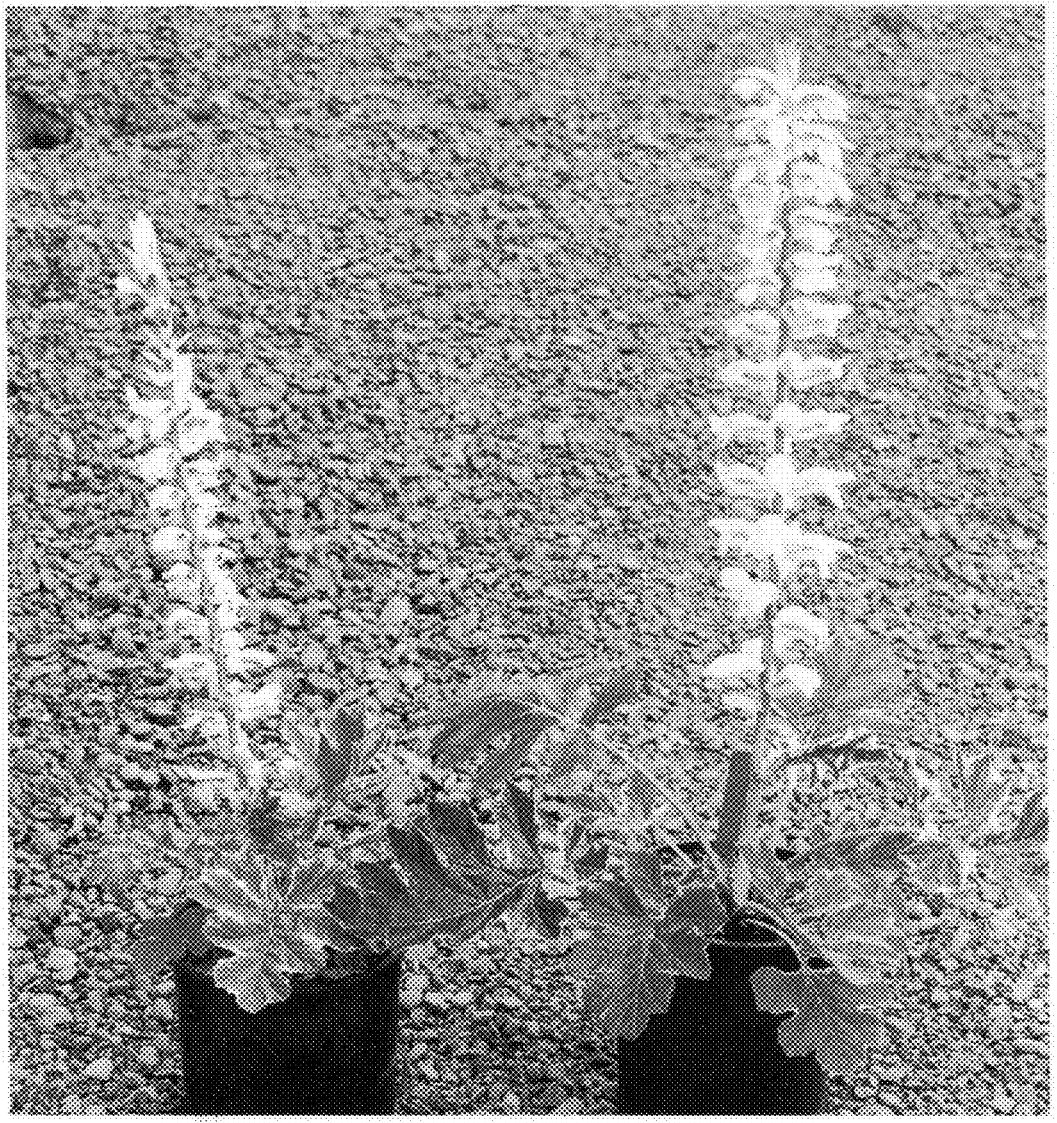
FIG. 1 shows side by side 9 month old specimens of *Acanthus* TASMANIAN ANGEL® (on the left) and *Acanthus* 'Whitewater' (on the right) for comparison of their size and vigor at the same age.
Figure 2:
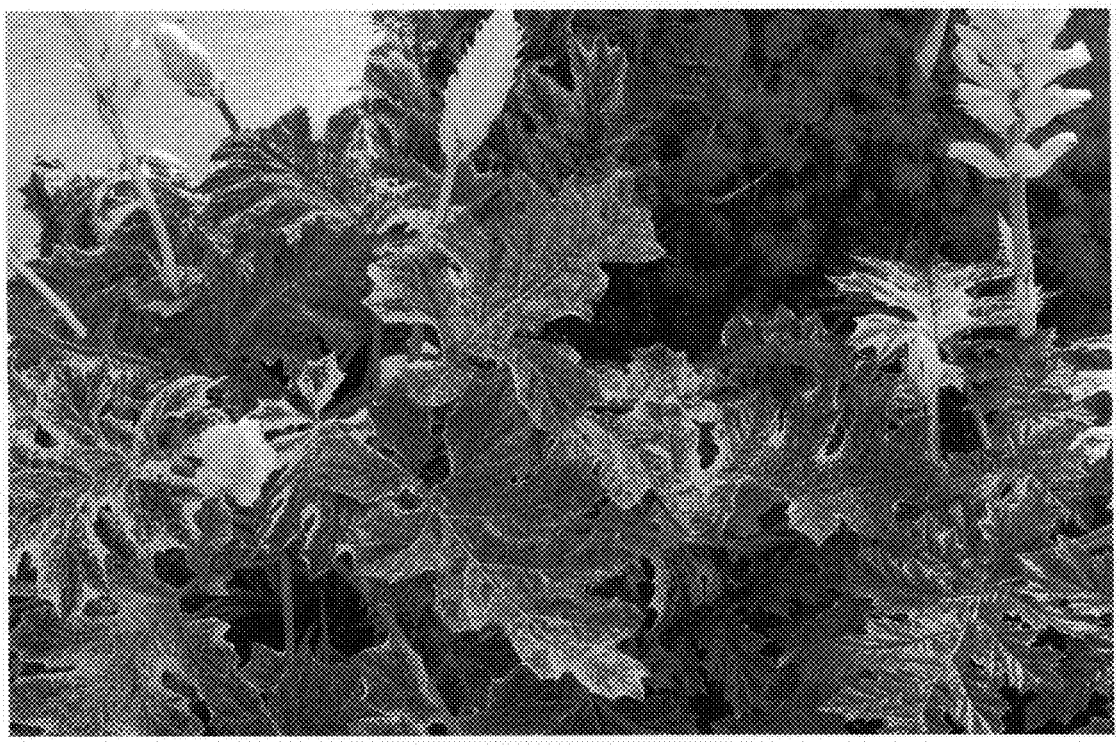
FIG. 2 shows two, two-year-old *Acanthus* 'Whitewater' growing in two gallon containers in spring in Canby, Oreg.

The following is a detailed description of the new *Acanthus* cultivar based on observations sixteen-month-old one gallon plants grown in a cool greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $3^{rd}$ edition.

Plant:

*Form.*—Clumping rosette, herbaceous perennial.

*Cold hardiness.*—USDA Zone 7-11.

*Size.*—Grows to 52 cm wide and 55 cm tall to the top of the flowers.

*Vigor.*—Excellent.

Leaf:

*Type.*—Simple.

*Arrangement.*—Basal rosette.

*Blade size.*—Grows to 23 cm long and 17.5 cm wide.

*Shape.*—Ovate, pinnatifid with lobes oblong, toothed, softly spiny.

*Venation.*—Pinnate.

*Margins.*—Coarsely spinose-serrate.

*Apex.*—Acute.

*Base.*—Cordate.

*Surface texture.*—Glabrous on top side and pubescent on veins on bottom side and along margin.

*Petiole description.*—Grows to 14 cm long and 6 mm wide, pubescent, Yellow Green 145B.

*Leaf color.*—Top side Green 137A with a variable amount of mottled variegation (strongest on the margins), White 155A, bottom side Yellow Green 146A with less mottled variegation than on the topside, White 155A.

Inflorescence:

*Type.*—Bracteate long stalked spike with flowers opposite.

*Number of flowers.*—Up to 50 per spike.

*Size of inflorescence.*—Grows to 40 cm tall and 9 cm wide.

*Peduncle.*—Grows to 55 cm tall and 6 mm wide, pubescent, Green Yellow 1D below the flowers and Greyed Purple 186A with the flowers.

*Pedicel.*—None.

*Bracts.*—Prominent, 1 large below each flower, cupped, ovate, irregularly and sparsely spinose-lacerate, tip spinose, base obtuse, grows to 32 mm long and 19 mm wide without the spinous lacerations which can each grow to 10 mm long and 2 mm wide at the base, pubescent on margins and bottom side, topside glabrous, Yellow White 158C with veins and top ¼ tinted Red Purple 70B on top and bottom side; 2 lateral bracts lanceolate, entire, acuminate, 16 mm long and 1.5 mm wide, Yellow White 158C with vein Red Purple 70B.

Flower bud:

*Size.*—20 mm long and 12 mm wide at the widest point prior to opening.

*Description.*—Tubular.

*Surface texture.*—Short pubescence.

*Color.*—Yellow 4D with tints of Red 36D.

Flower:

*Type.*—Zygomorphic, bisexual, borne in 4 ranks.

*Shape.*—Short tubular, lower lip three lobed.

*Size.*—42 mm long and 19 mm wide.

*Corolla description.*—40 mm long and 19 mm wide, short tube 3 mm long and 6 mm wide and a 3 lobed lower limb, lobes entire, 5 mm deep and 7 mm wide, obtuse, lateral lobes folded somewhat, tube and central lobe limb White 155A, lateral lobe limbs and lobes White 155A with Red Purple 70B prominent on veins and tinting the rest on top and bottom side, bottom side glabrous, inside sparsely pubescent.

*Calyx description.*—Irregularly 4 parted, upper sepal obovate, irregularly spinose on top, sides entire, base 7 mm wide, grows to 48 mm long and 15 mm wide, cupped, Yellow White 158C with veins and top ⅓ tinted Red Purple 70B on top and bottom side; lower sepal oblong, 32 mm long and 10 to 12 mm wide, longitudinally folded in half, sides entire, tip shallowly 2 lobed acute, base clasping, Yellow White 158C very lightly tinted Red Purple 70B near top; lateral sepal lobes ovate, 6 mm long and 5 mm wide, entire, obtuse, attenuate, Yellow White 158C.

*Pistil description.*—35 mm long, ovary 6 mm long and 4 mm wide, Yellow 4C, style 30 mm long, stigma and style Yellow White 158A.

*Stamen description.*—4 in number, filaments 19 mm long, White 155A tinted Red Purple 70A, anthers 8 mm long, Greyed Orange 175B, White 155D and brush-like when dehiscent, pollen none.

*Fragrance.*—None.

*Lastingness.*—A spike blooms for about 5 weeks on the plant.

*Bloom period.*—May through June in Canby, Oreg.

Fruit: None.

Seed: None, sterile.

Pests and diseases: *Acanthus* are susceptible to powdery mildew and fungal and bacterial leaf spots. The new cultivar has no known resistances but has shown no problems in Canby, Oreg.

I claim:

1. A new and distinct form of *Acanthus* plant substantially as shown and described.

* * * * *